United States Patent
Chung et al.

(10) Patent No.: US 10,053,466 B2
(45) Date of Patent: Aug. 21, 2018

(54) PROCESS FOR PREPARING CHIRAL DIPEPTIDYL PEPTIDASE-IV INHIBITORS

(71) Applicant: Merck Sharp & Dohme Corp., Rahway, NJ (US)

(72) Inventors: John Y. L. Chung, Edison, NJ (US); Feng Peng, Edison, NJ (US); Yonggang Chen, Westfield, NJ (US); Amude Mahmoud Kassim, Fairless Hills, PA (US); Cheng-yi Chen, Princeton, NJ (US); Mathew Maust, Manville, NJ (US); Mark McLaughlin, Summit, NJ (US); Michael J. Zacuto, Jersey City, NJ (US); Qinghao Chen, Edison, NJ (US); Lushi Tan, Edison, NJ (US); Zhiguo Jake Song, Edison, NJ (US); Yang Cao, Scotch Plains, NJ (US); Feng Xu, Staten Island, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/831,895

(22) Filed: Dec. 5, 2017

(65) Prior Publication Data
US 2018/0093992 A1    Apr. 5, 2018

Related U.S. Application Data

(62) Division of application No. 15/325,100, filed as application No. PCT/US2015/040674 on Jul. 16, 2015, now Pat. No. 9,862,725.

(60) Provisional application No. 62/026,763, filed on Jul. 21, 2014.

(51) Int. Cl.
C07D 487/04    (2006.01)
A61K 31/4162   (2006.01)

(52) U.S. Cl.
CPC ........ *C07D 487/04* (2013.01); *A61K 31/4162* (2013.01)

(58) Field of Classification Search
None
See application file for complete search history.

(56) References Cited

U.S. PATENT DOCUMENTS

| | | | |
|---|---|---|---|
| 5,041,442 A | 8/1991 | Romero et al. | |
| 5,869,670 A | 2/1999 | Hong et al. | |
| 8,431,564 B2 | 4/2013 | Timmers et al. | |
| 9,187,488 B2 | 11/2015 | Zacuto et al. | |
| 2005/0032804 A1 | 2/2005 | Cypes et al. | |
| 2010/0120863 A1 | 5/2010 | Biftu et al. | |
| 2010/0234607 A1 | 9/2010 | Jung et al. | |

FOREIGN PATENT DOCUMENTS

| | | |
|---|---|---|
| CN | 1429805 A | 7/2003 |
| CN | 1438211 A | 8/2003 |
| CN | 101031300 A | 9/2007 |
| WO | WO2002076450 A1 | 10/2002 |
| WO | WO2003000180 A2 | 1/2003 |
| WO | WO2003000181 A2 | 1/2003 |
| WO | WO2003004498 A1 | 1/2003 |
| WO | WO2003082817 A2 | 10/2003 |
| WO | WO2004007468 A1 | 1/2004 |
| WO | WO2004032836 A2 | 4/2004 |
| WO | WO2004037169 A2 | 5/2004 |
| WO | WO2004043940 A1 | 5/2004 |
| WO | WO2004050022 A2 | 6/2004 |
| WO | WO2004058266 A1 | 7/2004 |
| WO | WO2004064778 A2 | 8/2004 |
| WO | WO2004069162 A2 | 8/2004 |

(Continued)

*Primary Examiner* — Kamal Saeed
(74) *Attorney, Agent, or Firm* — Janet E. Fair; Catherine D. Fitch

(57) ABSTRACT

A process for preparing a compound of structural Formula Ia:

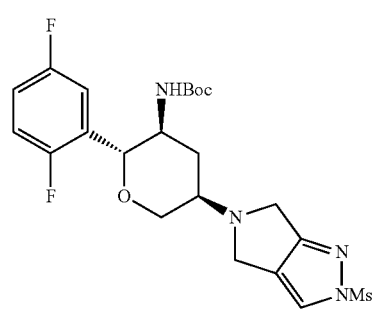

comprising Boc deprotection with TFA of:

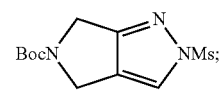

and
reductive amination of:

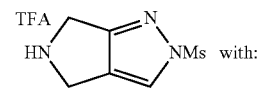

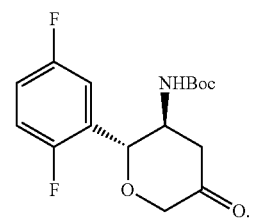

5 Claims, No Drawings

(56) References Cited

FOREIGN PATENT DOCUMENTS

| WO | WO2004103276 A2 | 12/2004 |
|---|---|---|
| WO | WO2004110436 A1 | 12/2004 |
| WO | WO2004112701 A2 | 12/2004 |
| WO | WO2005011581 A2 | 2/2005 |
| WO | WO2005044195 A2 | 5/2005 |
| WO | WO2005108382 A1 | 11/2005 |
| WO | WO2005116029 A1 | 12/2005 |
| WO | WO2006009886 A1 | 1/2006 |
| WO | WO2006023750 A2 | 3/2006 |
| WO | WO2006039325 A2 | 4/2006 |
| WO | WO2006065826 A2 | 6/2006 |
| WO | WO2006078676 A2 | 7/2006 |
| WO | WO2006104997 A2 | 10/2006 |
| WO | WO2006119260 A2 | 11/2006 |
| WO | WO2006127530 A2 | 11/2006 |
| WO | WO2007024993 A2 | 3/2007 |
| WO | WO2007035198 A2 | 3/2007 |
| WO | WO2007070434 A2 | 6/2007 |
| WO | 2007078726 A2 | 7/2007 |
| WO | WO2007087231 A2 | 8/2007 |
| WO | WO2007097931 A2 | 8/2007 |
| WO | WO2007126745 A2 | 11/2007 |
| WO | WO2007136603 A2 | 11/2007 |
| WO | WO2008060488 A1 | 5/2008 |
| WO | WO2009025784 A1 | 2/2009 |
| WO | WO2010056708 A1 | 5/2010 |
| WO | WO2011028455 A1 | 3/2011 |
| WO | WO2011037793 A1 | 3/2011 |
| WO | WO2011146358 A1 | 11/2011 |
| WO | WO2013003250 A1 | 1/2013 |
| WO | WO2014013076 A1 | 1/2014 |
| WO | WO2014018355 A1 | 1/2014 |
| WO | WO2014061031 A1 | 4/2014 |

PROCESS FOR PREPARING CHIRAL DIPEPTIDYL PEPTIDASE-IV INHIBITORS

CROSS-REFERENCE TO RELATED APPLICATIONS

This application is a divisional of U.S. application Ser. No. 15/325,100 which is a U.S. National Phase application under 35 U.S.C. § 371 of PCT Application No. PCT/US15/040674, filed Jul. 16, 2015, which published as WO2016/014324 A1 on Jan. 28, 2016, and claims priority under 35 U.S.C. § 365(b) from U.S. provisional patent application No. 62/026,763, filed Jul. 21, 2014.

FIELD OF THE INVENTION

The present invention is directed to a novel process for the preparation of omarigliptin, (2R,3S,5R)-2-(2,5-difluorophenyl)-5-[2-(methylsulfonyl)-2,6-dihydropyrrolo[3,4-c]pyrazol-5(4H)-yl]tetrahydro-2H-pyran-3-amine, a dipeptidyl peptidase-IV (DPP-4) inhibitor, for the treatment of Type 2 diabetes, and related intermediates.

BACKGROUND OF THE INVENTION

Syntheses of omarigliptin have previously been described in PCT international patent applications numbers WO 2010/056708 and WO2013/003250. The process described in WO 2010/056708 does not result in a favorable yield of the compound of structural Formula Ia, as it results in a racemic mixture. WO2013/003250 describes the following scheme to make the compound of structural Formula Ia, an intermediate for synthesizing omarigliptin:

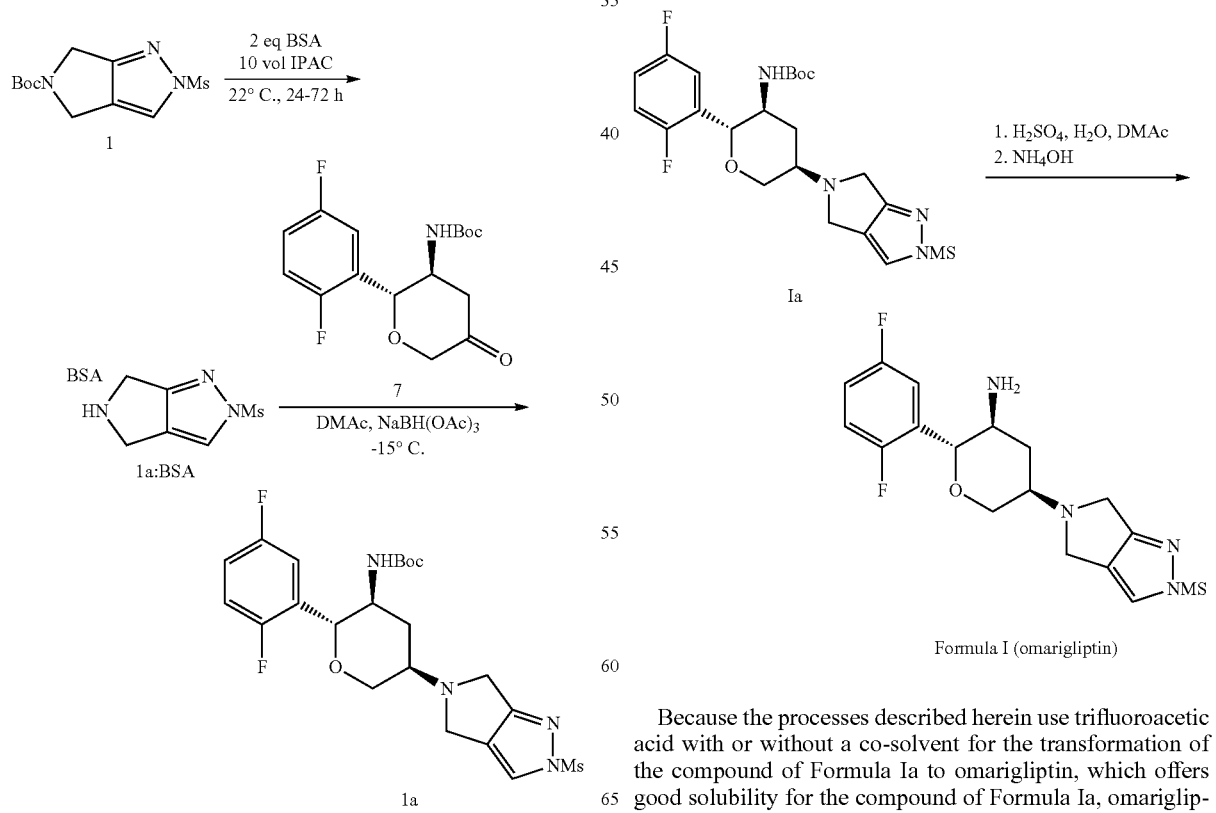

In WO2013/003250, synthesis of the compound of structural Formula Ia involves using benzenesulfonic acid (BSA) to remove the Boc protecting group of the compound of structural Formula 1, by first forming a BSA salt of the compound of structural Formula 1a. The BSA salt is then isolated and undergoes reductive amination with Boc-ketone of the compound of structural Formula 7, to produce the compound of structural Formula Ia, as a 19:1 diastereomeric mixture. The BSA mediated Boc deprotection requires up to 72 h to reach full conversion.

An alternative process which eliminates the need to isolate the BSA salt of the compound of Formula 1a and reduces the overall reaction time of the process is desired. The inventors have now discovered a process for making the compound of structural Formula Ia which eliminates the step of isolating a salt of the compound of structural Formula 1a and reduces the overall reaction time. The present process also produces an end-of reaction homogeneous solution via reductive amination, which facilitates crystallization of the compound of structural Formula Ia. The described process also improves the diastereoselectivity, overall yield, cost and cycle time over the process described in WO2013/003250.

WO2013/003250 also describes the Boc deprotection of the compound of Formula Ia to produce omarigliptin (Formula I) shown below. As described in WO2013/003250, the Boc deprotection of the compound of Formula Ia involves aging the substrate in aqueous sulfuric acid in DMAc at 30° C. for 15-20 h, then working up with ammonium hydroxide. This work up produces large amounts of poorly soluble ammonium sulfate which co-crystallizes with the desired product. As a result, isolation of the desired product requires a long cycle time for filtration, washing and drying.

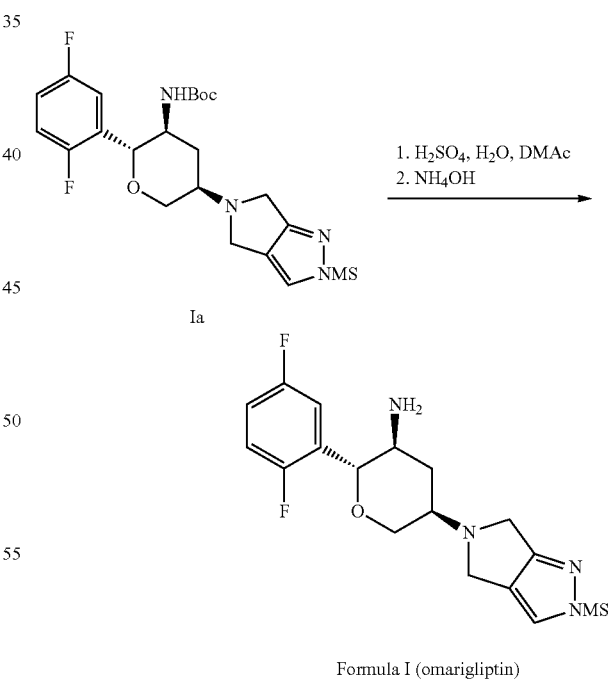

Formula I (omarigliptin)

Because the processes described herein use trifluoroacetic acid with or without a co-solvent for the transformation of the compound of Formula Ia to omarigliptin, which offers good solubility for the compound of Formula Ia, omarigliptin is achieved with fast reaction kinetics and good purity profiles.

SUMMARY OF THE INVENTION

Described herein are processes for preparing the compounds of structural Formula Ia and Formula I:

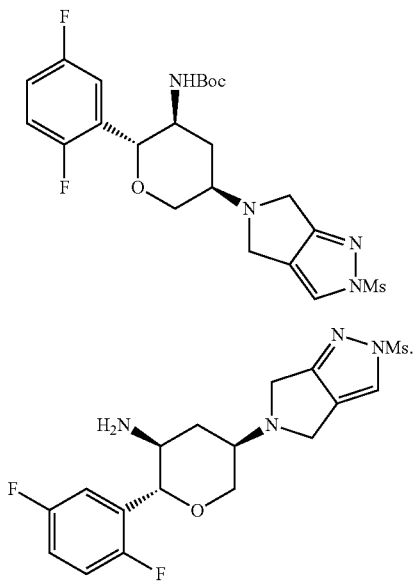

DETAILED DESCRIPTION OF THE INVENTION

One aspect of the present invention is concerned with a process for preparing a compound of structural Formula I:

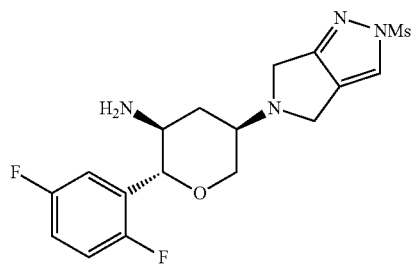

which comprises deprotecting a compound of structural Formula Ia:

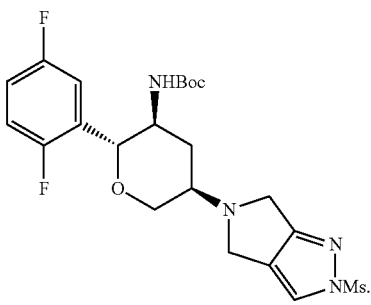

Another aspect of the invention is concerned with a process for preparing the compound of structural Formula Ia, wherein the process comprises a one-pot, two step through process comprising trifluoroacetic acid (TFA) Boc-deprotection of a Boc-mesyl-pyrazole and reductive amination with a Boc-ketone as shown below:

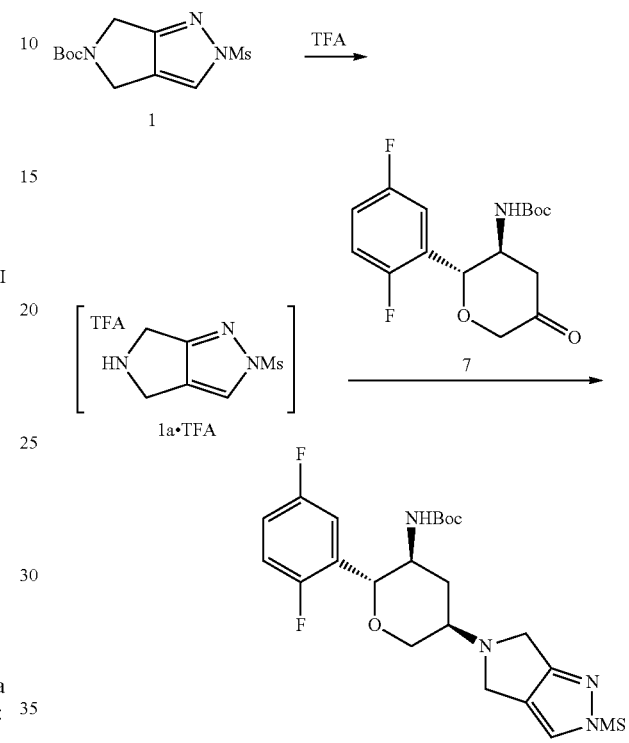

Described herein is a process for preparing a compound of structural Formula Ia:

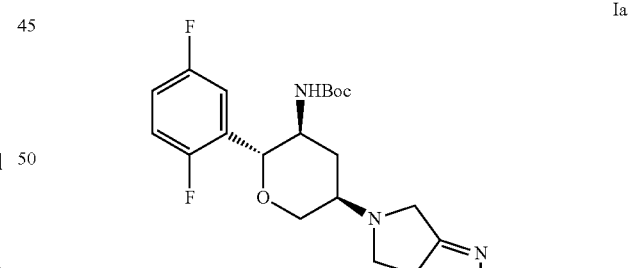

comprising Boc deprotection with TFA of a compound of structural Formula 1:

and
reductive amination of:

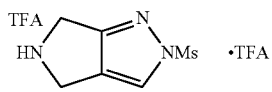

·TFA with a compound of structural Formula 7:

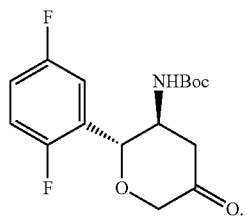

In certain embodiments, the process is done as a through process, meaning that the process proceeds from the starting materials of compounds of structural Formula 1 and Formula 7, to the compound of Formula Ia or Formula I with no isolation of any intermediates.

In certain embodiments, the process described herein further comprises the step of crystallizing Formula Ia. Crystallization of the compounds can be done using methods known in the art.

The amount of TFA used in the process described herein should be enough to allow the reaction to occur. The amount of TFA used can be between about 1-5 volumes. The term "volume" used herein refers to 1 ml of TFA to 1 g of the starting material, which in the process described herein is optionally the Boc protected mesyl pyrazole. In certain embodiments, the amount of TFA used is about 2-5 volumes. In other embodiments the amount of TFA used is about 3-5 volumes. In still other embodiments, the amount of TFA used is about 1 volume. In still other embodiments, the amount of TFA used is about 2 volumes. In still other embodiments, the amount of TFA used is about 3 volumes. In still other embodiments, the amount of TFA used is about 4 volumes. In still other embodiments, the amount of TFA used is about 5 volumes.

In specific embodiments, the TFA used is neat, meaning void of any water or other co-solvent. However, a solvent system comprising TFA and a co-solvent may be used. In certain embodiments, a solvent system comprising at least 90% of TFA and a co-solvent can be used. In certain embodiments, a solvent system comprising about 90-99.9% of TFA and a co-solvent can be used. In certain embodiments, the co-solvent can be present in an amount of between about 0.1-10%. Examples of co-solvents include, but are not limited to, water and DMAc.

One feature of the process for preparing the compound of structural Formulas Ia and I described herein, is that the presently described process results in improved yields of the compound of structural Formula Ia and I as compared to previously known processes. In certain embodiments, the yield of the compound of structural Formula Ia and I is at least about 80% by weight. In other embodiments, yield of the compound of structural Formula Ia and I is at least about 85% by weight. In other embodiments, yield of the compound of structural Formula Ia and I is at least about 90% by weight. In other embodiments, yield of the compound of structural Formula Ia and I is at least about 95% by weight.

Another feature of the processes for preparing the compound of Formula Ia and I, described herein is that the presently described process results in molecules of improved diastereomeric selectivity as compared to previously known processes. In certain embodiments, the diastereomeric selectivity is at least 20:1. In other embodiments, the diastereomeric selectivity is at least 25:1. In still other embodiments, the diastereomeric selectivity is about 30:1.

Also described herein are processes for preparing a compound of structural Formula I. In certain embodiments described herein, the process of preparing a compound of structural Formula I:

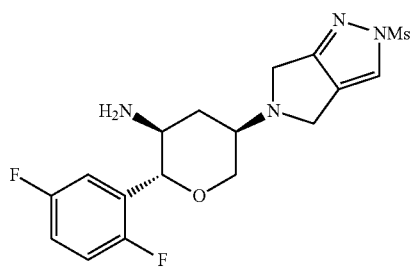

comprising Boc deprotection with TFA of a compound of structural Formula 1:

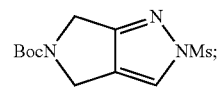

reductive amination of:

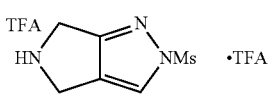

·TFA with a compound of structural Formula 7:

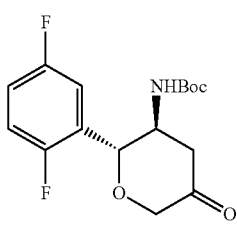

which results in the compound of structural Formula Ia:

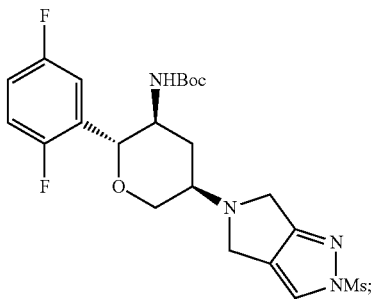

and
removing the Boc group of the compound of structural Formula Ia.

Additionally, in certain embodiments, the process of preparing the compound of Formula I may further include crystallizing the compound of Formula Ia prior to removing the Boc protecting group.

Also described herein are processes for preparing compounds of Formula 1 and Formula 7, which are used as intermediates for preparing compounds of Formula I and Formula Ia:

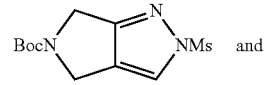

In certain embodiments, the compound of structural Formula 1 is prepared by the following processes:

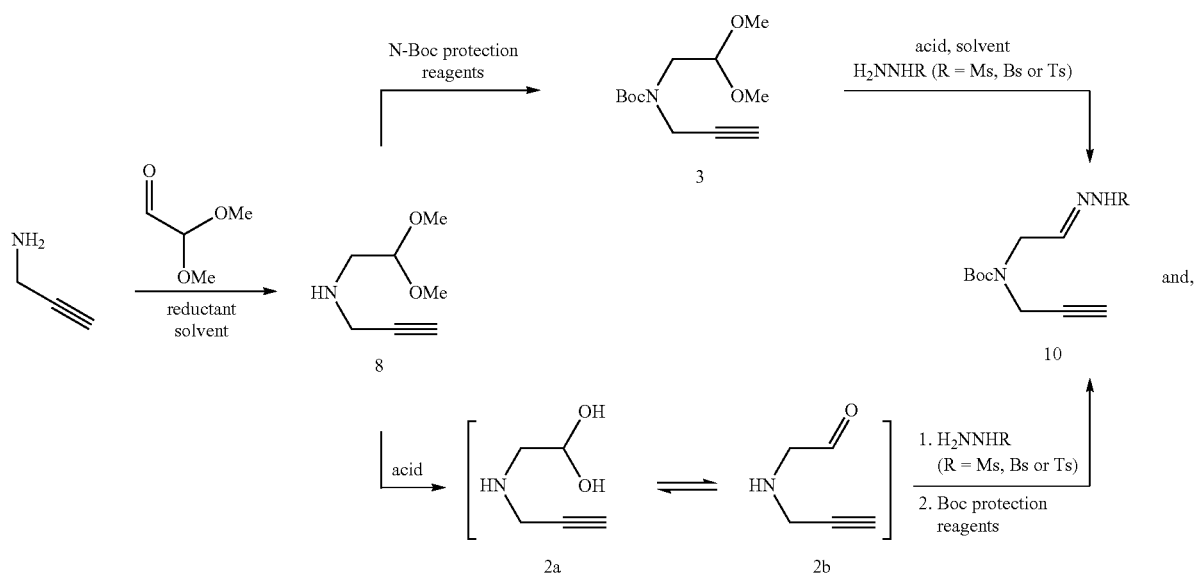

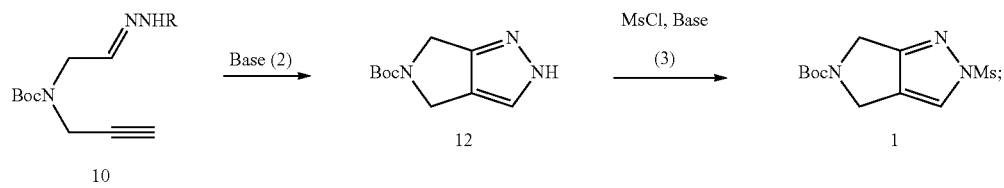

or alternatively

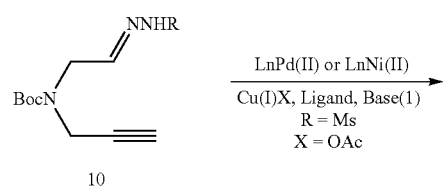

-continued

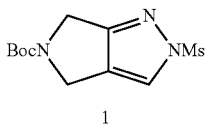

In certain embodiments of the processes described herein, the compound of Formula 1 is prepared by the following: first, Compound 10 is prepared from reductive amination of propargyl amine and glyoxal dimethyl acetal, followed by hydrolysis of dimethyl acetal in the presence of an acid, then hydrazone formation with mesyl, besyl or tosylhydrazide ($H_2NNHR$, wherein R=Ms, Bs or Ts). Treatment of Compound 10 with a base, and optionally solvent at 40-80° C. affords Compound 12 which is taken on to the compound of Formula 1. Each step forming an independent aspect of the present invention, is discussed in detail below.

Step 1:

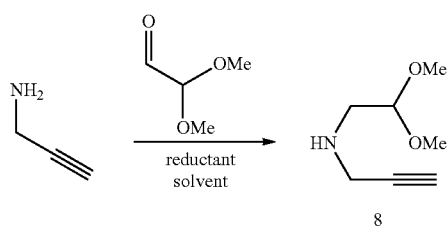

In certain embodiments, to arrive at Compound 8, a reductant was added to a mixture of glyoxal dimethyl acetal and propargyl amine in a solvent. Suitable reductants include, but are not limited to, sodium triacetoxyborohydride (STAB) and sodium borohydride/alkyl or aryl carboxylic acid mixtures. A preferred reductant is STAB. Suitable solvents include but are not limited to, ethanol, methanol, amyl alcohol, ethylene glycol, THF, methyl tertiary-butyl ether (MTBE), dioxane, toluene, dichlorobenzenes, dichloromethane, methyl tetrahydrofuran (MeTHF), acetone, ethyl acetate (EtOAc), acetone, dimethylformamide (DMF), dimethyl sulfoxide (DMSO), N-methylpyrrolidone (NMP), N,N-dimethylacetamide (DMAc), acetonitrile (MeCN), dichloroethane (DCE) and isopropanol. A preferred solvent is THF.

Step 2:

In certain embodiments, to arrive at Compound 10 via Compound 3 (2,2-dimethoxyacetaldehyde), Compound 8 is added to N-Boc protection reagents. Suitable Boc protection reagents include, but are not limited to, Boc-anhydride which can be added under basic conditions.

When Compound 8 is added to N-Boc protection reagents in the above step, N-Boc protection reagents can optionally be in a solvent. Suitable solvents, include, but are not limited, ethanol, methanol, amyl alcohol, ethylene glycol, THF, methyl tertiary-butyl ether (MTBE), dioxane, toluene, dichlorophenyl, dichloromethane, methyl tetrahydrofuran (MeTHF), acetone, ethyl acetate (EtOAc), acetone, dimethylformamide (DMF), dimethyl sulfoxide (DMSO), N-methylpyrrolidone (NMP), N,N-dimethylacetamide (DMAc), acetonitrile (MeCN), dichloroethane (DCE) and isopropanol. A preferred solvent is THF.

To a solution of Compound 3 in solvent, a weak or buffered acid is added. Suitable acids include, but are not limited to, acetic acid, $FeCl_3$, and other Lewis acids. After pH adjustment, mesyl, besyl or tosyl hydrazide ($H_2NNHR$, wherein R=Ms, Bs or Ts) is then added. Suitable solvents, include, but are not limited to, ether, ethanol, methanol, amyl alcohol, ethylene glycol, dimethoxyethane (DME), THF, methyl tertiary-butyl ether (MTBE), dioxane, toluene, dichlorophenyl, dichloromethane, methyl tetrahydrofuran (MeTHF), acetone, ethyl acetate (EtOAc), acetone, dimethylformamide (DMF), dimethyl sulfoxide (DMSO), N-methylpyrrolidone (NMP), N,N-dimethylacetamide (DMAc), acetonitrile (MeCN), dichloroethane (DCE) and isopropanol. Preferred solvents include either:DME, DME:water or MeCN:water.

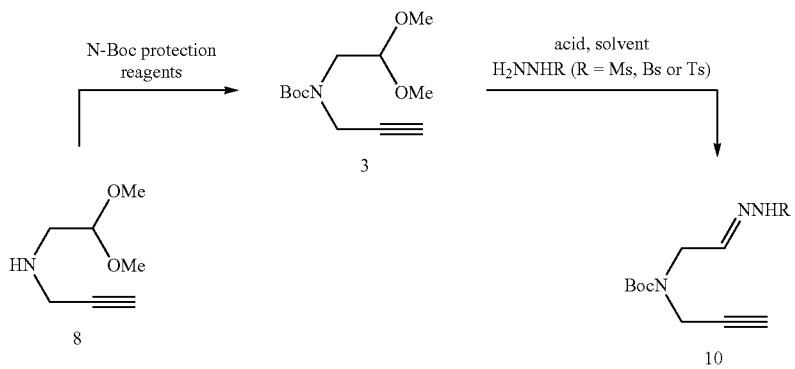

Step 2a:

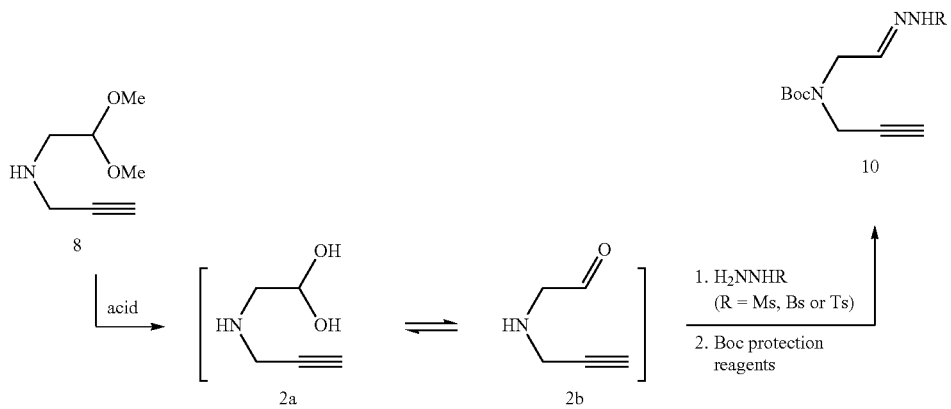

Alternatively, Compound 10 can be synthesized via Compounds 2a/2b, by adding Compound 8 to acid. Suitable acids include, but are not limited to, sulfuric acid, trifluoroacetic acid, HBr, HCl, $R^5SO_3H$ wherein $R^5$ is hydrogen, $C_{1-6}$ alkyl, $C_{3-6}$ cycloalkyl or aryl. Unless otherwise indicated, the term "$C_{1-6}$ alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like. Unless otherwise indicated, the term "$C_{3-6}$ cycloalkyl" means cycloalkyls having 3 to 8 carbons, forming one or more carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like. Unless otherwise indicated, the term "aryl" includes phenyl, naphthyl, tolyl, and the like.

In certain embodiments, HCl is preferred. Mesyl, besyl or tosyl hydrazide ($H_2NNHR$, wherein R=Ms, Bs or Ts) is then added. After pH adjustment, then Boc protection reagents are added. Suitable Boc protecting agents include, but are not limited to, $Boc_2O$.

Step 3:

-continued

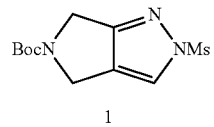

In certain embodiments, to arrive at Compound 1, Compound 10 was added to Base(2) and optionally solvent and the reaction was heated above room temperature. Suitable Base(2) includes, but is not limited to, potassium phosphate ($K_3PO_4$), $K_2CO_3$, $KHCO_3$, $Na_2CO_3$, $NaHCO_3$, $K_2HPO_4$, $Na_3PO_4$, $Na_2HPO_4$, and $NaHCO_3$. Suitable solvents include, but are not limited to, toluene, THF, DMAc, hydrazine, EtOH and isopropyl acetate (IPAC).

A solution of mesyl chloride, Base(3) and optionally solvent is added to arrive at the compound of Formula 1. Base(3), that can be used with the processes above includes, but is not limited to, sodium or potassium bis(trimethylsilyl) amide, $K_2CO_3$, 1,1,3,3-tetramethylguanidine (TMG), triethylamine, 1,8-diazabicyclo[5.4.0]undec-7-ene (DBU), alkoxide bases (such as KOtBu) and cesium carbonate ($Cs_2CO_3$). Solvents that can be used with the processes above include, but are not limited to, toluene, tert-amyl alcohol, DMF, DMAC, 2-MeTHF and THF.

Alternatively, the compound of Formula 1 is prepared by the following process where the mesyl group was retained. Compound 10 is added to a metal catalyst, copper salt, ligand, base and oxidant in solvent affords compound of Formula 1.

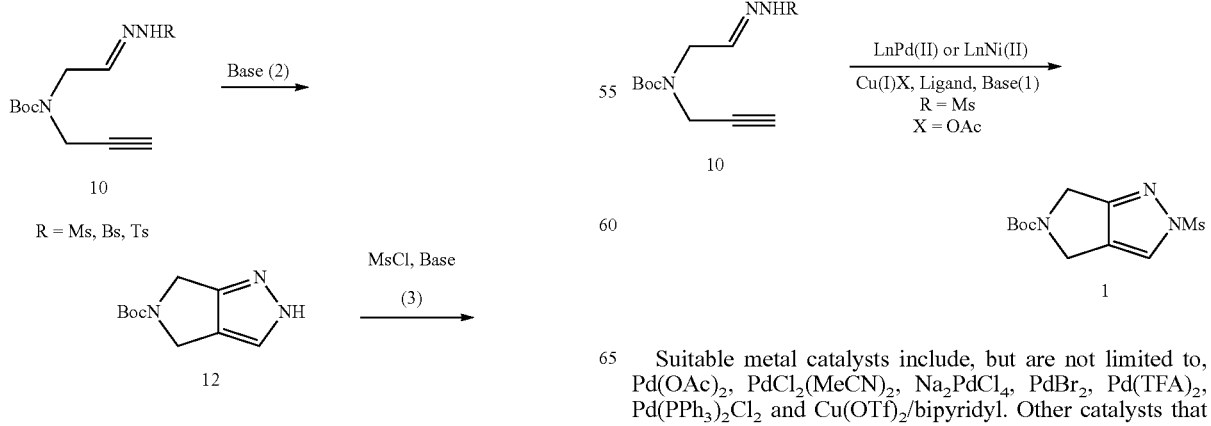

Suitable metal catalysts include, but are not limited to, $Pd(OAc)_2$, $PdCl_2(MeCN)_2$, $Na_2PdCl_4$, $PdBr_2$, $Pd(TFA)_2$, $Pd(PPh_3)_2Cl_2$ and $Cu(OTf)_2$/bipyridyl. Other catalysts that can be used in the process above include, but are not limited to, PdCl$_2$, (PPh$_3$)$_2$PdCl$_2$, (2,2'-bispyridyl)PdCl$_2$, Pd(OAc)$_2$, PdBr$_2$, Na$_2$PdCl$_4$, Pd(TFA)$_2$, NiCl$_2$, Ni(OAc)$_2$, Ni(acac)$_2$, NiBr$_2$-DME, Pd(OAc)$_2$ or PdCl$_2$ in conjunction with various mono- or bidentate phosphine ligands. Examples of these ligands include, but not limited to, P(o-tolyl)$_3$ (tri-orthotolyl phosphine), P(furyl)$_3$ (trifuryl phosphine), P(Cy)$_3$ (tricyclohexyl phosphine), P(C$_6$F$_5$)$_3$ (triperfluorophenylphosphine), dppe (diphenylphosphino ethane), dppp (diphenylphosphino propane), dppb (diphenylphosphino butane), dppf (diphenylphosphino ferrocene), Josiphos, X-Phos and CataXium. Other ligands that can be used as catalysts in the process above include, but are not limited to, various bis-amine ligands, including, but not limited to, TMEDA (N,N,N',N'-tetramethylethylene diamine), DMEDA (N,N'-dimethylethylene diamine), 2,2'-bis-pyridine, substituted 2,2'-bis-pyridine, 2,2',2"-tris-pyridine, substituted 2,2',2"-tris-pyridine, phenanthroline and substituted phenanthroline. Various bis-heteroatom ligands include, but are not limited to, quinoline, dimethylglycine, proline, picolinic acid, thiophene carboxylic acid, N,N-disubstituted salicylamide, various bis-imines of cyclohexyldiamine and various 1,3-dicarbonyl substrates.

Suitable copper salts that can be used in the process above include, but are not limited to, CuCl, CuCl$_2$, Cu(OAc)$_2$, Cu(I)(OAc), CuBr, CuBr$_2$, Cu(OTf), Cu(OTf)$_2$.

Suitable bases that may be used as Base(1) include, but are not limited to, K$_3$PO$_4$, K$_2$CO$_3$, KHCO$_3$, Na$_2$CO$_3$, NaHCO$_3$, K$_2$HPO$_4$, Na$_3$PO$_4$, Na$_2$HPO$_4$, and NaHCO$_3$.

Suitable solvents that can be used in the process above include, but are not limited to, toluene, DMAc, THF, tert-amyl alcohol, EtOH and IPAC.

Suitable oxidants that can be used in the process above include, but are not limited to, tert-butyl hydrogen peroxide (TBHP), air, O$_2$, tert-butyl perbenzoate (tBuOOBz), tert-butyl peracetate (tBuOOAc), benzoquinone, benzoyl peroxide and sodium percarbonate.

In other embodiments of the processes described herein, the compound of Formula 12 is prepared by the following process:

In such embodiments, hydrogenation of keto nitrile, Compound 13, using Raney Ni, Pd or Pt catalyst in methanol or aqueous methanol in the presence of a short chain dialkylamine (R$_2$NH, wherein R=C$_1$-C$_6$ alkyl including but not limited to Me, Et, nPr, branched alkyls and cycloalkyls) affords Compound 14, which upon treatment with hydrazine (hydrate) affords Compound 15. In another embodiment, Compound 13 can be converted to Compound 15 directly by substituting hydrazine for the short chain dialkylamine during the hydrogenation of keto-nitrile 13. Subsequent treatment with pTsOH or MsOH affords Compound 12.

In certain embodiments, the compound of Formula 7 is prepared by the following process:

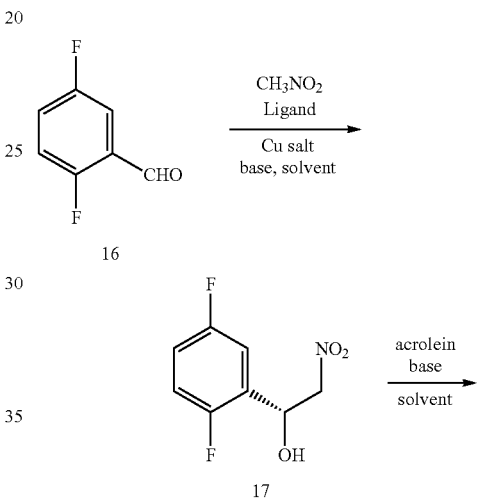

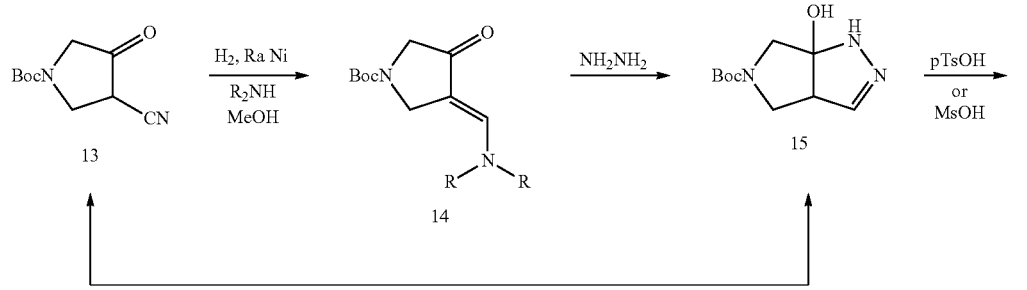

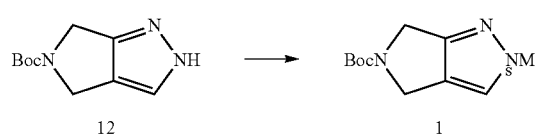

15
-continued

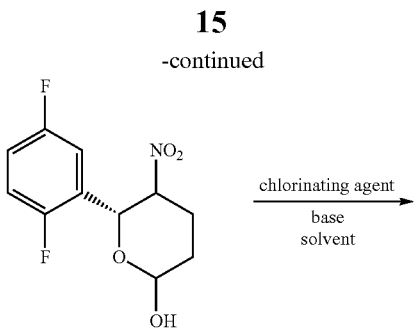

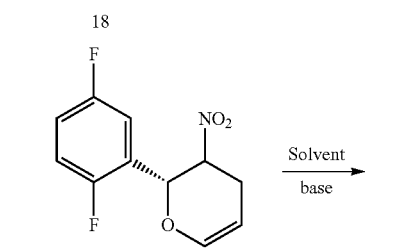

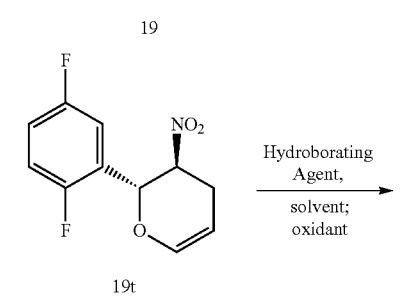

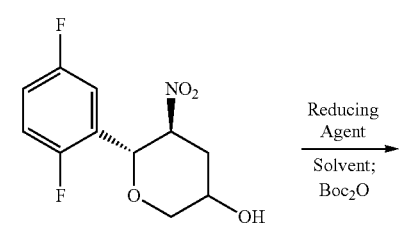

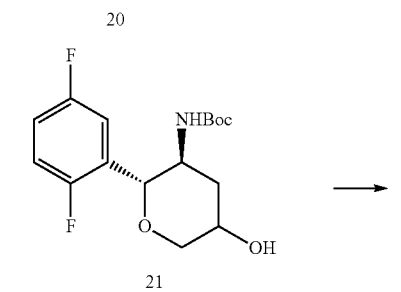

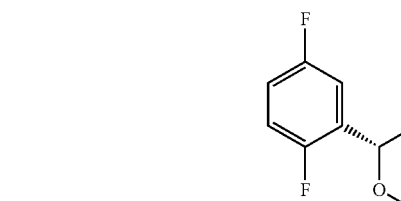

The compound of structural Formula 7 can by prepared by the following steps, each step of which forms an independent aspect of the present invention:

16

Step 1:

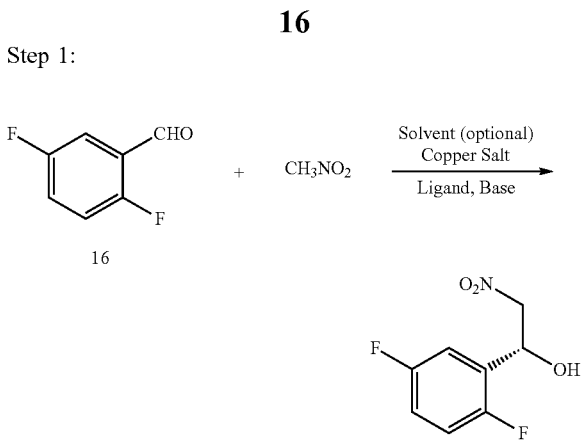

With regard to Step 1, Compound 16 is added to copper salt, ligand and a base. To that nitromethane was added. The described reaction can be run without solvent or with solvents. Suitable optional solvents that can be used include, but are not limited to, ethanol, methanol, amyl alcohol, ethylene glycol, THF, methyl tertiary-butyl ether (TBME), dioxane, toluene, dichlorophenyl, dichloromethane, methyl tetrahydrofuran (MeTHF), acetone, ethyl acetate (EtOAc), acetone, dimethylformamide (DMF), dimethyl sulfoxide (DMSO), N-methylpyrrolidone (NMP), N,N-dimethylacetamide (DMAc), acetonitrile (MeCN), dichloroethane (DCE) and isopropanol.

Suitable copper salts (both Cu(I) and Cu(II)) that can be used include, but are not limited to, copper benzoate, copper propionate, copper 2-Et-hexanoate, copper acetate, copper trifluoroacetate, copper triflate, copper S-prolinate, copper picolinate and copper halides. In certain embodiments, copper acetate or copper propionate (Cu(propionate)$_2$) or copper chloride are used. In certain embodiments, copper chloride is preferred.

Suitable ligands include, but are not limited to,

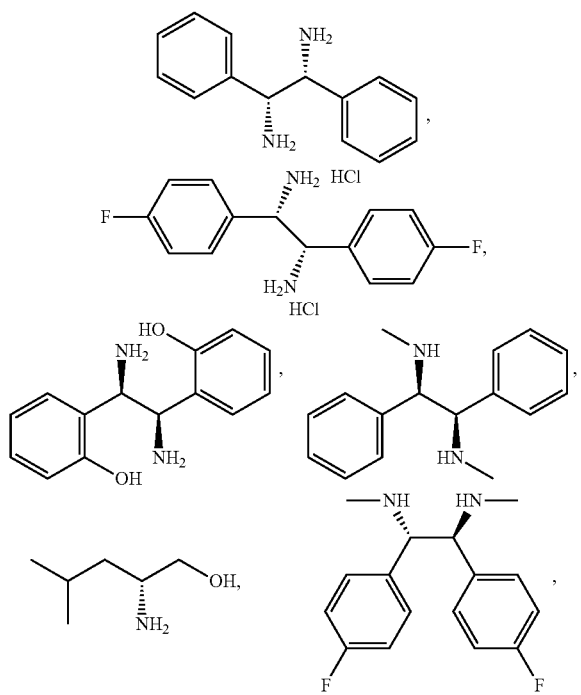

-continued

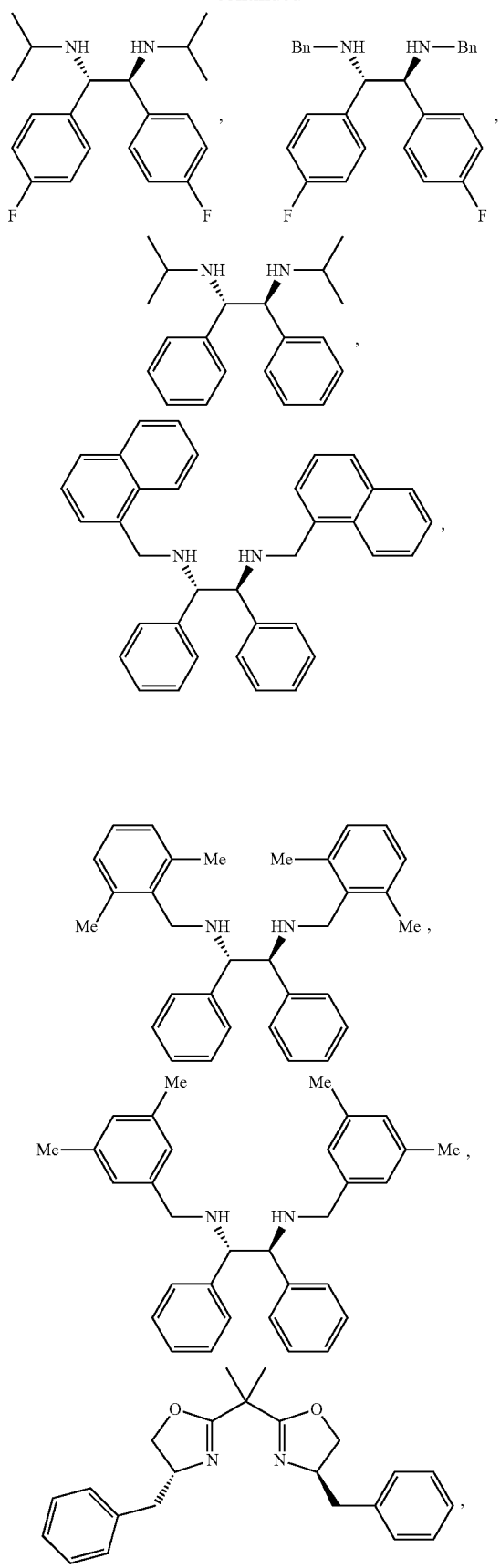

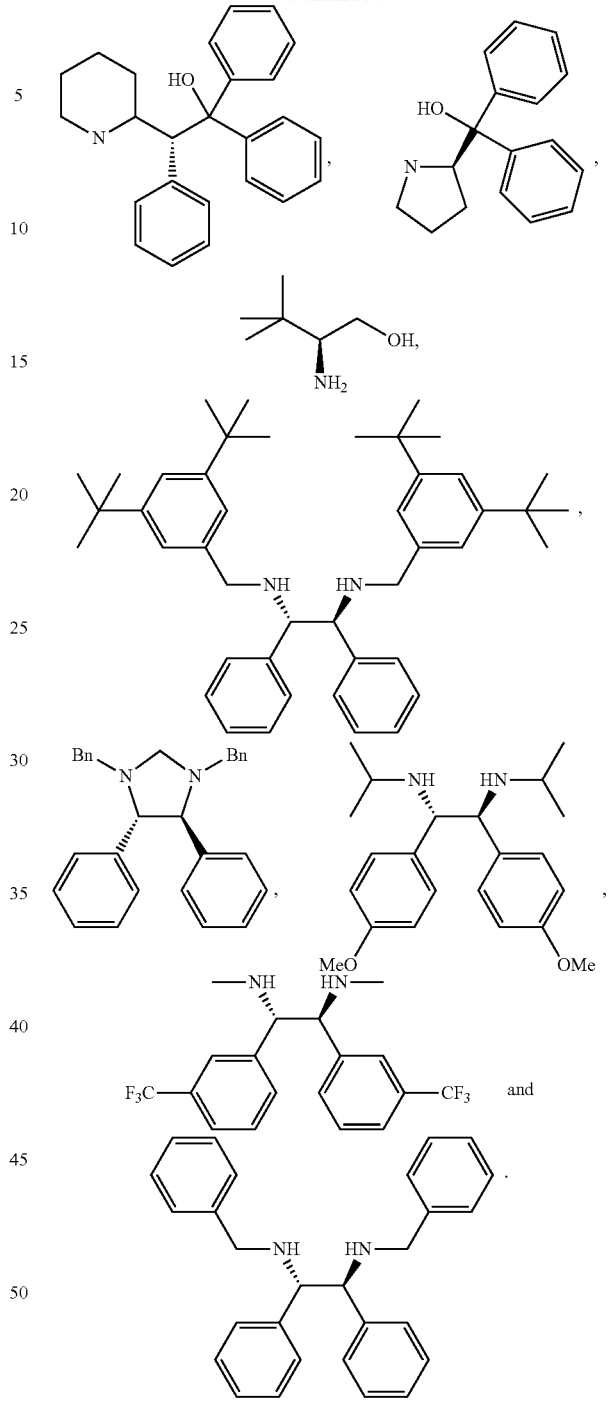

Suitable bases include, but are not limited to, 1,4-diazabicyclo[2.2.2]octane (DABCO), hexamethylenetetramine, 2,4,6-tri-tert-buylpyridine, julolidine, N,N-dimethylpiperazine, 5-methylpiperidine, N-methyl-piperidine, N-methylpyrrolidine, N-ethyldicyclohexylamine, N-methyldicyclohexylamine, triisopropylamine, 1-aminoadamantane, di-n-butylamine, dicyclohexylamine, triethylamine, 5-methyldiethylenetriamine, methylguanidine, dimethylaminopyridine, quinidine, and quinulidine. In certain embodiments, DABCO or N,N-dimethylpiperizine is used. The reaction can afford Compound 17 in up to about 95% yield. In certain embodiments, the reaction affords Compound 17 in about 90-95% yield and about 89-94% ee after aqueous work up with EDTA disodium solution, and brine.

It should be noted that Compound 16 can be replaced with any aldehyde with functional groups that can be converted to the 2,5-difluoro intermediate at any point in the reaction scheme.

Step 2:

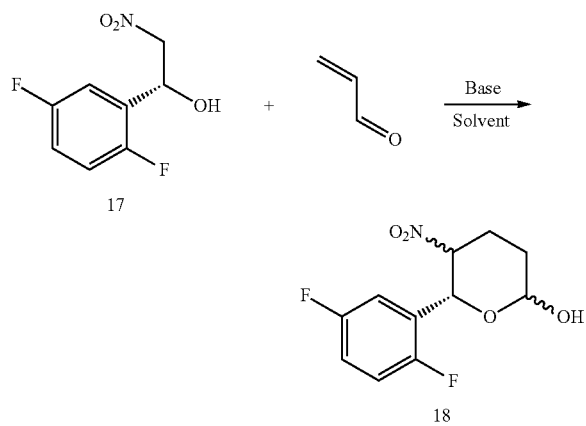

Concerning Step 2, acrolein is added to Compound 17 in base and solvent. Suitable bases include but are not limited to, N,N-diisopropylethylamine (DIPEA). Suitable solvents include but are not limited to, tetrahydrofuran. Step 2 could be carried out with or without aqueous work up of 18.

Step 3:

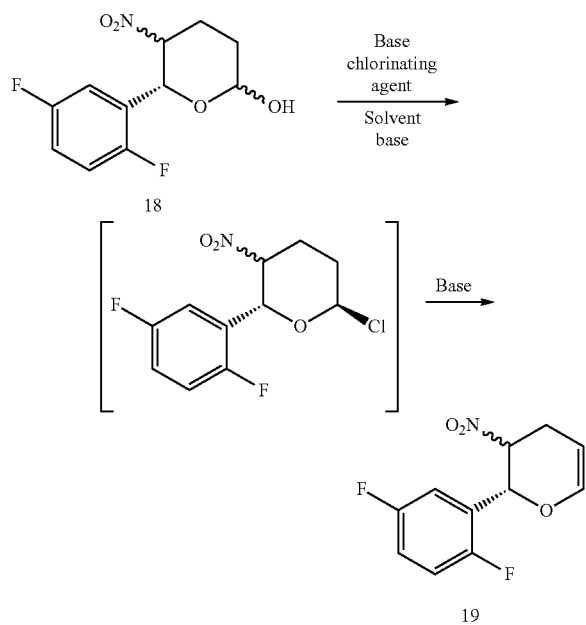

With regard to Step 3, Compound 18 in base is added to a base for chlorination, chlorinating agent and solvent. Solvents that can be used include, but are not limited to, tetrahydrofuran (THF), methyl tertiary-butyl ether (TBME), dioxane, toluene, dichlorobenzene, dichloromethane, methyl tetrahydrofuran (MeTHF), acetone, ethyl acetate (EtOAc), dimethylformamide (DMF), dimethyl sulfoxide (DMSO), N-methylpyrrolidone (NMP), N,N-dimethylacetamide (DMAc), acetonitrile (MeCN), dichloroethane (DCE), and mixtures thereof. In certain embodiments the solvent is acetonitrile. Suitable chlorinating agents include, but are not limited to, mesyl chloride, diethyl chlorophosphate, thionyl chloride and cyanuric chloride. A particular suitable chlorinating agent for the process is MsCl.

Suitable bases for chlorination include, but are not limited to, 1,1,3,3-tetramethylguanidine (TMG), cesium carbonate ($Cs_2CO_3$), potassium phosphate ($K_3PO_4$), sodium carbonate ($Na_2CO_3$), potassium carbonate ($K_2CO_3$), triethylamine (TEA), 1,4-diazabicyclo[2.2.2]octane (DABCO), 4-dimethylaminopyridine (DMAP), 1,8-diazabicyclo[5.4.0]undec-7-ene (DBU) and Hunig's base ($iPr_2NEt$). In certain embodiments, a suitable base for the chlorination process is $iPr_2NEt$ or triethylamine.

After the reaction is complete a dehydrochlorination base is added. Suitable bases for dehydrochlorination include, but are not limited to pyridine, N,N-dimethylaniline, collidines, lutidines, N-methyl morpholine, Hunig's base, tri-n-butylamine and triethylamine. A particularly suitable base for the process is 2,3,5-collidine.

Suitable reaction temperatures for chlorination are $-10$-+$10°$ C. Suitable dehydrochlorination temperatures are +20-$50°$ C.

Step 4:

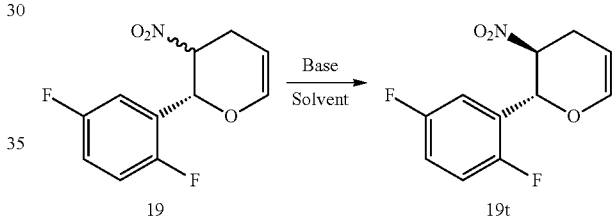

With regard to Step 4, Compound 19 is added to a solvent and base. Solvents that can be used include, but are not limited to, ethanol, methanol, tetrahydrofuran (THF), methyl tertiary-butyl ether (TBME), dioxane, dimethoxyethane (DME), toluene, dichlorobenzene, dichloromethane, methyl tetrahydrofuran (MeTHF), cyclopentyl methyl ether (CPME), acetone, ethyl acetate (EtOAc), isopropyl acetate (IPAC), dimethylformamide (DMF), dimethyl sulfoxide (DMSO), N-methylpyrrolidone (NMP), N,N-dimethylacetamide (DMAc), acetonitrile (MeCN), dichloroethane (DCE), n-propanol, isopropanol, butanols, amyl alcohols, water and mixtures thereof. In certain embodiments, the solvent is a mixture of water and isopropanol.

Suitable bases include, but are not limited to, 1,1,3,3-tetramethylguanidine (TMG), cesium carbonate ($Cs_2CO_3$), potassium phosphate ($K_3PO_4$), sodium carbonate ($Na_2CO_3$), potassium carbonate ($K_2CO_3$), triethylamine (TEA), 1,4-diazabicyclo[2.2.2]octane (DABCO), 4-dimethylaminopyridine (DMAP), 1,8-diazabicyclo[5.4.0]undec-7-ene (DBU), potassium tert-butoxide (KOtBu), Hunig's base ($iPr_2NEt$), morpholine, N-methyl morpholine, imidazole, s-collidine, pyridine and diisopropylamine. A particularly suitable base for the process is triethylamine.

Step 5:

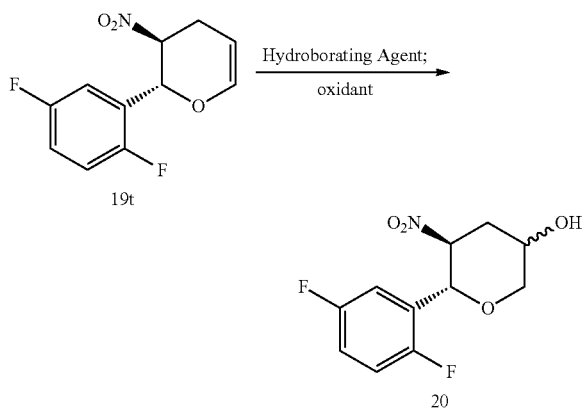

In Step 5, a hydroborating agent and oxidant is added to Compound 19t in solvent. Solvents that can be used include, but are not limited to, tetrahydrofuran (THF), methyl tertiary-butyl ether (TBME), dioxane, dimethoxyethane (DME), toluene, dichlorophenyl, dichloromethane, methyl tetrahydrofuran (MeTHF) and cyclopentyl methyl ether (CPME). In certain embodiments the solvent is TBME. Suitable hydroborating agents include, but are not limited to, borane reagents such as, borane THF complex, borane dimethyl sulfide (DMS) complex and $NaBH_4/BF_3$ etherate (or THF). Suitable oxidants include, but are not limited to, sodium perborate, sodium percarbonate, hydrogen peroxide and hydrogen peroxide urea complex.

Step 6:

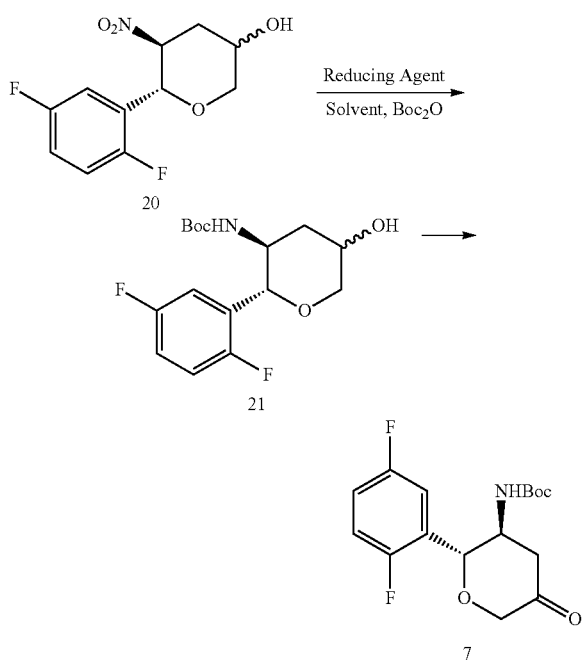

With regard to Step 6, Compound 20 was reduced to the amine with a reducing agent in solvent. Optionally, Step 6 can be performed in the presence of an acid. Suitable reducing agents that can be used include, but are not limited to, zinc powder and zinc powder in a solvent with acid, under hydrogenative conditions with catalysts such as Raney nickel, Pt, or Pd. Solvents that can be used include, but are not limited to, ethanol, methanol, propanol, isopropanol, tetrahydrofuran (THF), dioxane, N,N-dimethylacetamide (DMAc), acetonitrile (MeCN), water and mixtures thereof. In certain embodiments, the solvent is ethanol or THF. Suitable optional acids include but are not limited to, sulfuric acid, trifluoroacetic acid, HBr, HCl, $R^5SO_3H$ wherein $R^5$ is hydrogen, $C_{1-6}$ alkyl, $C_{1-6}$ cycloalkyl or aryl. Additionally, after complete reduction of the nitro to the amine, the mixture can be treated with a base, such as $K_2CO_3$, $Na_2CO_3$, NaOH or KOH, followed by Boc anhydride to give Compound 21. Compound 7 is obtained from compound 21 via oxidation as described in WO2013/003250.

Representative experimental procedures utilizing the novel process are described below. However, the invention is not limited to the specific reactants and reaction conditions in the example described below.

Abbreviations

Boc=tert-butyloxycarbonyl
Bs=besyl, benzenesul
BSA=benzenesulfonic acid
DABCO=1,4-diazabicyclo[2.2.2]octane
DBU=diazobicyclo undecene
DMF=dimethylformamide
DMAc=N,N-Dimethylacetamide
DMAP=4-Dimethylaminopyridine
DMSO=dimethyl sulfoxide
EDTA=ethylenediaminetetraacetic acid
ee=enantiomeric excess
EE=ethyl
EtOH=ethanol
EtOAc=ethyl acetate
h=hour(s)
HPLC=high-performance liquid chromatography
$K_2CO_3$=potassium carbonate
KOH=Potassium hydroxide
IPA=isopropyl alcohol
L=liter(s)
Me=methyl
MeCN=acetonitrile
MeTHF=methyl tetrahydrofuran
min=minute(s)
mL=milliliter(s)
Ms=mesyl, methanesulfonyl or $CH_3SO_2$—
MTBE=methyl tert-butyl ether
$NaHCO_3$=sodium bicarbonate
$Na_2SO_4$=Sodium sulfate
$NaBH(OAc)_3$=Sodium triacetoxyborohydride
NMP=N-methylpyrrolidone
nPr=N-propyl
r.t.=room temperature
TBME=methyl tertiary-butyl ether
TEA=triethylamine
Tf=trifluoro
TFA=trifluoroacetic acid
THF=tetrahydrofuran
TMG=tetramethyl guanidine
Ts=p-toluenesulfonyl
v=volume(s)

Certain starting materials and reagents are either commercially available or known in the chemical scientific or patent literature. Purification procedures include, for example, distillation, crystallization, and normal or reverse phase high performance liquid chromatography.

SCHEME 1: Synthesis of Boc Mesyl-Pyrazole

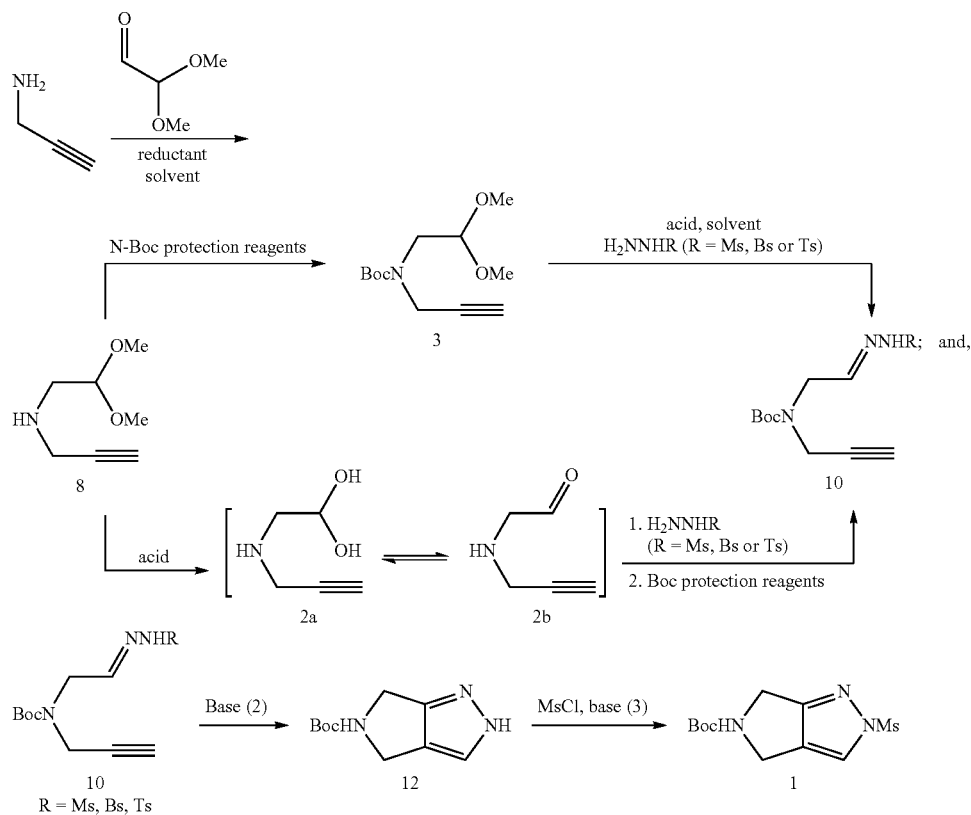

or alternatively

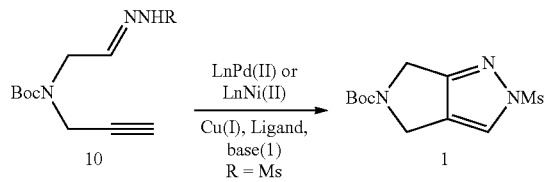

Compound 8

To a solution of propargyl amine (1.05 equivalent) in THF (15-20 volume), glyoxal dimethyl acetal aqueous solution (1 equivalent) was added at 4° C. over 5 minutes. The resulting solution was aged at 0-2° C. for 10-15 minutes. Sodium triacetoxyborohydride was added in 3 portions (3×0.33 equivalents) over 3 hours, while maintaining the temperature between 3-15° C. in between the addition. The resulting mixture was aged for 10 hours. The reaction was quenched by adding cold water, followed by 10N solution of NaOH (5 equivalents) and MTBE (10 volumes). The biphasic layer was stirred vigorously and allowed to settle. The organic layer was separated, washed with aqueous NaCl solution (2×5 volumes) and azeotropically distilled to almost dryness to afford an orange oil, which was used directly in the next step.

Compound 10 Via Compounds 2a/2b

A solution of Compound 8 (1 equivalent) in concentrated HCl (4-5 equivalents) was stirred at room temperature for 20 hours and then concentrated in vacuo at 30-35° C. to remove half of its volume. Additional concentrated HCl solution (2 equivalents) was added to the resulting solution and the mixture was aged for another day at room temperature, diluted with MeCN (2 volume) and the pH was adjusted to 4 by adding 50 wt % aqueous NaOH solution. Mesyl hydrazide (1 equivalent) was then added as a solid, and the resulting solution was aged at room temperature overnight. Water (10 volumes) and EtOAc (15 volumes) was added, followed by $Boc_2O$ (1 equivalent) and solid $NaHCO_3$ to bring the pH to 6-7. Once gas evolution ceased (approximately 5 hours), the aqueous layer was separated, and the organic layer was washed with water (2 volumes) and brine (2 volumes) and concentrated. The crude product was then purified by column chromatography (DCM:EtOAc or Hex:EtOAc) to afford product 10.

Compound 3

To a solution of dimethylacetal amine 8 (1 equivalent) in MTBE (10 volumes) and water (3 volumes) Boc-ahydride (1.1 equivalents) was slowly added between 0-10° C. The pH was adjusted to 6-7 during the reaction by addition of solid $NaHCO_3$. After aging at room temperature for 5 hours, the organic layer was separated, washed two times with water (3 volume), brine and concentrated to give crude product, which was used directly in the next step.

Compound 10 Via Compound 3

To a solution of dimethylacetal Boc-protected amine (Compound 3) (1 equivalent) in MeCN:water (20 volumes) mesyl hydrazide (1.3 equivalents) was added, followed by 5 wt % $FeCl_3$ on $SiO_2$ gel (0.5 equivalent). The resulting slurry was aged at 45° C. for several days and filtered. The filtrate was treated with water (5 volumes) and extracted with EtOAc (15 volume). The organic layer was washed two times with water (5 volume) followed by 5 wt % aqueous NaHCO₃ solution and brine and azeoptroprically dried to give a crude mixture which was subjected to MTBE crystallization to afford the hydrazone compound 10.

Compound 12

To a solution of hydrazone (Compound 10 (1 equivalent)) in NMP (10 volumes), K₃PO₄ (4 equivalents) was added at room temperature and the resulting slurry was heated to 45-50° C. and aged for 25 hours. Ethyl acetate (20 volumes) was added, the mixture was washed with water (2×5 volume), and the organic layer was washed with brine, dried over Na₂SO₄, filtered and concentrated to give crude product.

Compound 1

NiBr₂.DME complex (0.05 equivalent), followed by Cu(I)OAc co-catalyst (0.05 equivalent), cyclohexyldiamine ligand (0.1 equivalent) and MeCN (20 volumes) was added to a flask. The resulting mixture was stirred for a couple of minutes and then treated with hydrazone (Compound 10 (1 equivalent)), K₃PO₄ (1 equivalent) and tert-butyl peracetate (tBuOOAc, 1.1. equivalent) as the oxidant. The resulting slurry was aged at 25-30° C. for 15 hours and then diluted with EtOAc (10 volumes) and water (5 volumes). The organic layer was separated, washed with 5% EDTA-Na₂ solution (5 volumes), 10% aqueous citric acid solution, 10% aqueous NaHCO₃ and brine. The final organic layer was then treated with resin (100 wt % loading with regard to starting Compound 10), aged for 3 hours at room temperature, filtered and concentrated in vacuo to afford crude Compound 1.

SCHEME 2: Alternative Synthesis of Boc Mesyl-Pyrazole

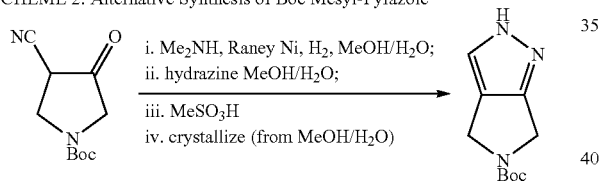

The keto-nitrile (20 g) was dissolved in MeOH (120 mL). A solution of 40 wt % aqueous dimethylamine (80 mL) was added, followed by Raney Ni (0.8 g). The solution was placed under an atmosphere of H₂ and heated to T$_i$=35° C. for 22 h. The reaction was then cooled to ambient temperature and the vessel was vented to remove excess H₂. The catalyst was removed via filtration, and the filtrate was subjected to constant volume distillation (at ~35° C. and 50 mm Hg partial pressure) with MeOH in order to remove excess dimethylamine. The resulting crude solution was carried forward.

The crude solution was heated to 40° C. A solution of 35% aqueous hydrazine (8.6 mL) was added over 30 min. One hour after the addition was complete, the solution was cooled to 22° C., at which point the pH of the resulting solution was 11.5.

Methanesulfonic acid (11.9 mL) was added slowly, with external cooling, maintaining 25-35° C. until the target pH=1.5-2 was reached. The resulting solution was aged an additional 18 h. The red solution was concentrated to remove MeOH. Upon cooling, crystallization commenced. Saturated aqueous NaHCO₃ (~6 mL) was added until pH=6.

The slurry was subjected to slow, careful concentration to remove ~30 mL of solvent from the supernatant. The resulting slurry was stirred for 1 h, after which loss to the supernatant was 7.2 mg/mL. The slurry was filtered. The cake was displaced with 1 cake volume of 5:95 MeOH:water (30 mL), then water (30 mL). The solid was dried for 3 h, after which the solid was collected.

SCHEME 3: Synthesis of the Boc Ketone

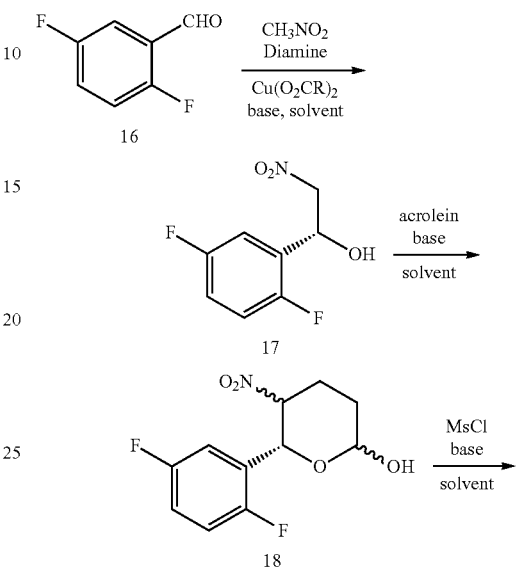

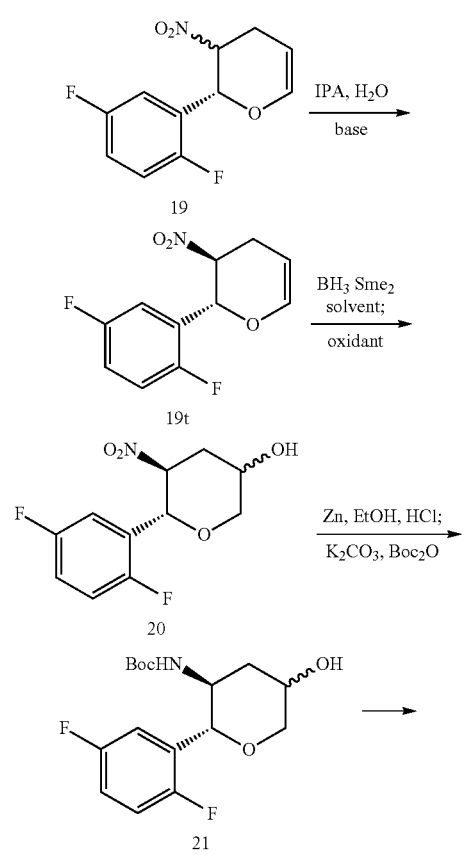

-continued

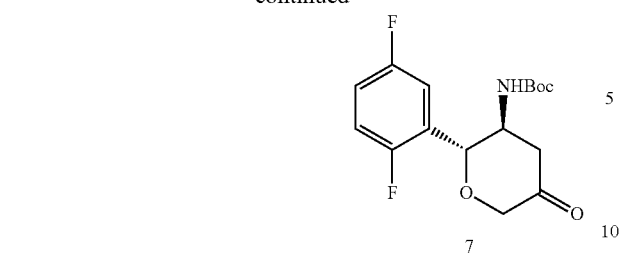

Step 1: Asymmetric Henry Reaction—(R)-1-(2,5-difluorophenyl)-2-nitroethanol (17)

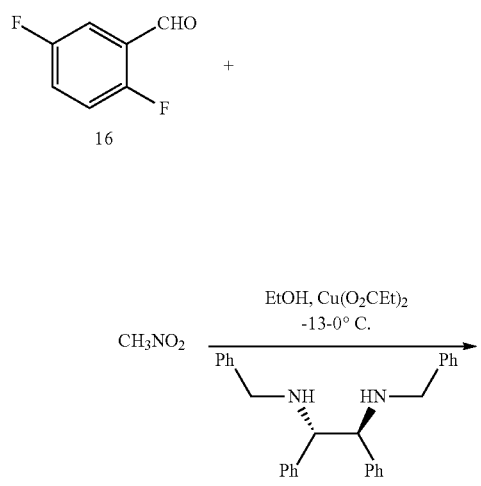

A round bottom flask was charged with ligand L (0.829 g), Cu(II) propionate monohydrate (0.402 g) (or Cu(II) acetate (0.31 g) or CuCl or CuCl$_2$) and EtOH (350 ml) and agitated at room temperature for 1 h. 2,4-Difluorobenzaldehyde (100.0 g) was added followed by DABCO (2.368 g) (or 2,4-dimethylpiperizine) and the mixture was cooled to −5-−15° C. Cold (0° C.) nitromethane (190 ml or 215 g) was added slowly to the cold solution and the solution was aged at −5 to −15° C. for 20-24 h and at 0° C. for 2-4 h. 5 wt % EDTA.2Na (500 ml) followed by water (200 mL) and MTBE (1.0 L) was added to the cold solution, and the temperature was raised to 20° C. The layers were separated and the organic layer was washed with additional 5 wt % EDTA.2Na (500 ml), followed by water (50 mL) and brine (250 mL). The organic layer, containing Compound 17, was concentrated to remove nitromethane, then the solvent was switched to THF.

Step 2: Michael-Lactolization—Nitro Lactol

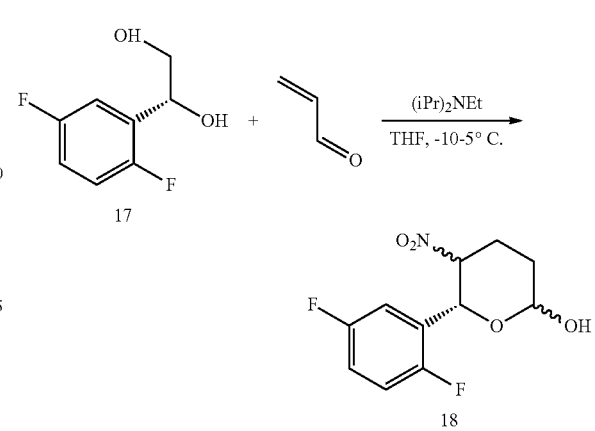

To Compound 17 in 2 volumes of THF (258 mL) from Step 1 under N$_2$ and cooling at 0° C., 1 equivalent of Hunig's base was added. 1.15 equivalents of acrolein was added over 1 h via syringe pump at 0-5° C. The reaction was stirred at −10-0° C. overnight. The resulting mixture was used directly in the next step.

Alternatively, the mixture was concentrated at 0-5° C. to remove excess acrolein, then the residue was flushed with acetonitrile until Hunig's base and water are mostly removed. The residue was taken up in 8 volumes of acetonitrile and used directly in the next step.

Alternatively, at the end of the reaction the mixture was worked up by diluting with MTBE and washing with aqueous citric acid solution, and aqueous NaHCO$_3$ solution, and the solvent was switched to acetonitrile. Alternatively, the end reaction mixture was taken forward directly to the next step.

Step 3: Dehydration—Nitro Dihydropyrans

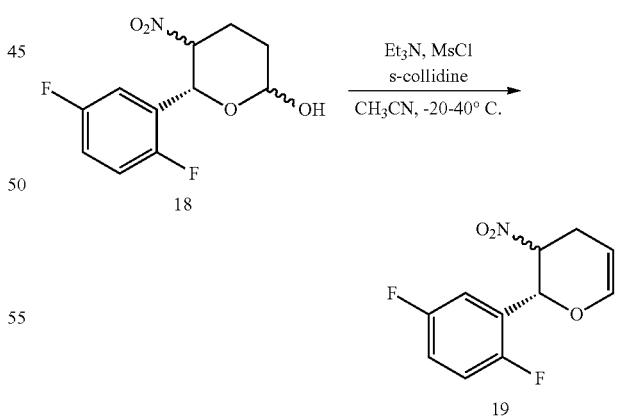

1.1 Equivalents of TEA was added to the acetonitrile solution of lactol 18 from Step 2 followed by 1.2 equivalents of mesyl chloride and 1.2 equivalents of S-collidine under <+10° C. The reaction was aged at 10° C. for 0.5-1 h. Alternatively, the end of the reaction mixture from Step 2 was cooled to between −20° C. to 0° C. Two equivalents of S-collidine and 1.4 equivalents of mesyl chloride were then added. The mixture was heated to 36° C. and aged overnight. The mixture was cooled to room temperature. 15 volumes of MTBE was added and the solution was washed with 3 volumes 10 wt % citric acid and 6 volumes water, 10 volumes water, then 3 volumes of 5% NaHCO$_3$ solution and 6 volumes water. The organic was concentrated with 20 volumes of MTBE using 10 volumes MTBE. The organic solution was stirred with 20-30 wt % AQUAGUARD for 2 hours at room temperature. The mixture was filtered and washed with 2 volumes of MTBE.

Step 4: Dynamic Kinetic Resolution (DKR) Crystallization—Trans-Nitro-Dihydropyran (19t)

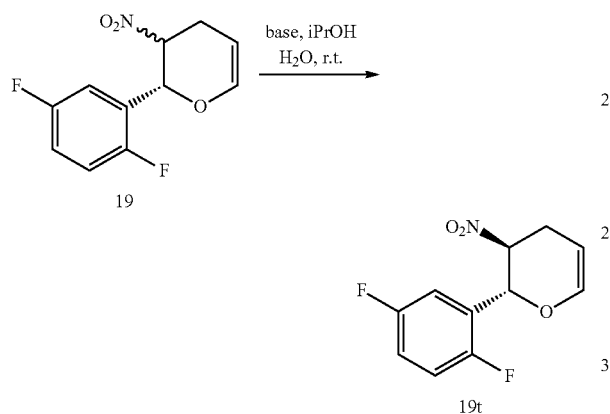

The organic MTBE solution of Step 3 was solvent switched to 2 volumes of IPA and the final volume was ~300 mL. 10 Mol % of TEA (or DABCO or morpholine or DMAP) was added. Then water (115 mL) was slowly added over 3 hours. The slurry was filtered, washed with 80/20 IPA/water (2×100 mL) and vacuum dried under N$_2$.

Step 5: Hydroboration/Oxidation—Trans-Nitro-Pyranol

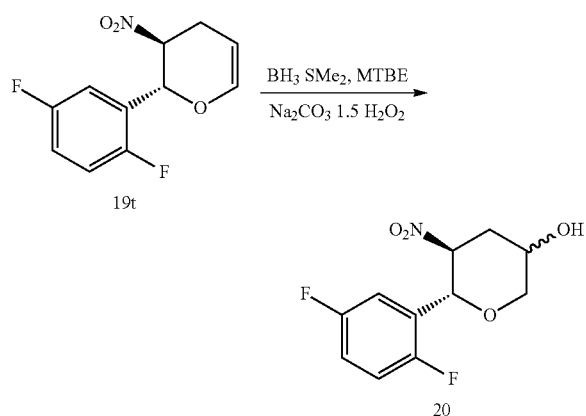

To a vessel charged with trans-nitro-dihydropyran (10 g), MTBE (100 mL) was added under nitrogen. The mixture was stirred at room temperature to give a clear orange solution. The solution was cooled to +2° C. and borane dimethyl sulfide complex (9.55 ml) was added. The clear solution was aged for 2-5 h until >99% conversion by HPLC analysis. The reaction was slowly quenched with water (7.25 ml) keeping at <+9° C. After the solution was aged at 5° C. for 5 min, water (78 mL) was added at <+13° C. Solid sodium percarbonate (13.26 g, 84 mmol) was added. The suspension was stirred at 5° C. for 15 h. The mixture was transferred to a separatory funnel with the aid of 60 mL MTBE and 20 mL water. The mixture was allowed to warm to room temperature. The aqueous phase was back-extracted with 40 mL MTBE. The combined organic phase was washed once with 30 mL half saturated sodium chloride solution, once with 15 mL brine and 15 mL 0.2N HCl, and once with 30 mL half-saturated sodium chloride solution. The organic layer was dried over Na$_2$SO$_4$. The organic was filtered, washed with 10 mL MTBE and concentrated to an oil. The oil was diluted to 200 mL for a 0.191M solution.

Step 6: Nitro Reduction/Boc Protection—Pyranol

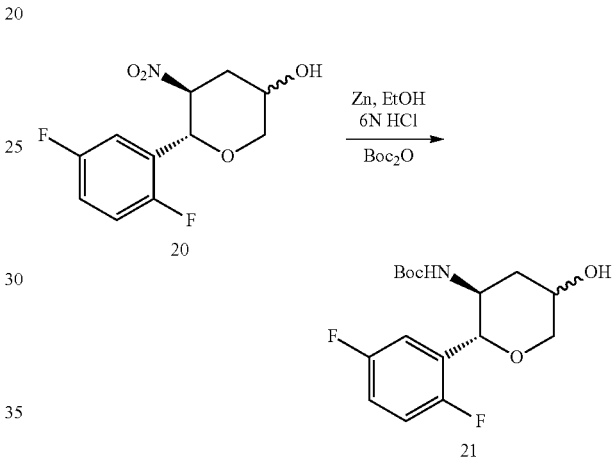

A 3-neck jacketed round bottom flask equipped with overhead stirrer was charged with 0.191M (5R,6S)-5-nitro-pyran-3-ol (119 ml) (Compound 20) in ethanol and ethanol (32 ml). The solution was cooled to 11-12° C. Cold 6N HCl (19.55 ml, 117 mmol) was added at <+17° C. Zinc dust (12.93 g) was added in five portions (5×2.59 g) at <+26° C. The mixture was stirred at 12° C. for 22 h. 1M K$_2$CO$_3$ (76 mL) was added in one portion. MTBE (59 mL) was added then EDTA 2K 2H$_2$O (22.55 g) was added over 10 min at <+14° C. To the solution 45 wt % KOH (4.86 mL) solution was added. The solution was cooled to 5° C., and 1.1 equivalents of Boc$_2$O (5.46 g) was added. The solution was rinsed with MTBE (10 mL) and stirred at 5° C. for 2 h, then at 12° C. for 16 h, and then at 24° C. for 10 h until >99.5% conversion. The solution was transferred to a separatory funnel with the aid of MTBE (30 mL) and water (5 mL). The organic layer was filtered and washed with MTBE (20 mL). The organic filtrate was concentrated. MTBE (60 mL), water (30 mL) and saturated sodium chloride solution (15 mL) were added. The mixture was warmed in a 30° C. bath to dissolve solid, and then concentrated. The concentrate was flushed with toluene in a 60° C. bath, then concentrated. Toluene (8.4 mL) was added and the mixture was heated to 80° C. Heptane (70.8 mL) was added over 1 h at 80° C., then cooled slowly to room temperature. The mixture was filtered and washed with 1:2 toluene/heptane (23.55 mL), filterated and vacuum dried under nitrogen until a constant weight.

The purity could be further upgraded by the following procedure: a round bottom flask was charged with the product of Step 6 (7.069 g) from above. EtOH (21 mL) was added and the mixture was heated to 45° C. Water (31.5 mL) was slowly added over 1 h at 45° C. The mixture was aged for 1 h. Water (31.5 mL) was added in one portion, then cooled slowly to room temperature and aged overnight. The slurry was filtered and washed with 1:3.5 EtOH/water (23.56 mL). Crystals were vacuum dried under nitrogen until a constant weight.

Alternatively, Compound 20 was reduced with 100 psi hydrogen in 20 volume wet THF in the presence of 10-30 wt % Raney nickel at 50° C. Then the reaction mixture was basified with 2 equivalent of $K_2CO_3$ and a slight excess $Boc_2O$ to afford crude Compound 21 after aqueous work up.

Compound 7 was obtained from 21 via oxidation as described in WO2013/003250.

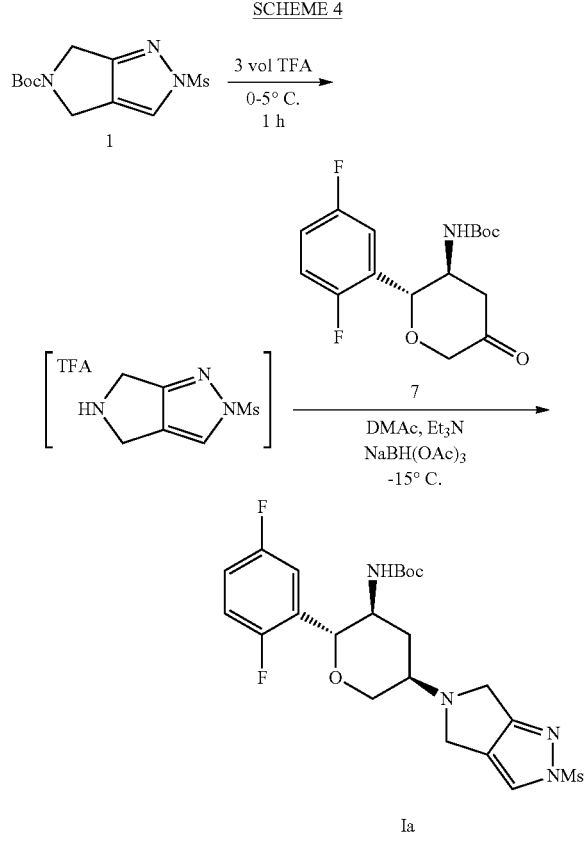

SCHEME 4

Boc-mesyl-pyrazole solid 1 was added to 2.5 volumes of TFA at 0-2° C., over 2-3 minutes under nitrogen, followed by 0.5 volume of TFA rinse. Conversion to TFA salt was complete within 0.5-1 h at 1-2° C. DMAc (14 vol) followed by triethylamine (5 equivalents or 2.3 volumes) were slowly added to the TFA reaction mixture at 0° C. maintaining <+20° C. Boc-ketone 7 (0.89 equivalent) was then added at −15° C. followed by solid $NaBH(OAc)_3$ (1.4 equivalents) which was added in three portions over 1 h. The reaction solution was aged at −15° C. overnight. The solution was then warmed to 22° C., and after aging for 2-5 h. Diastereomeric ratio was ≥96.5:3.5.

The solution was seeded with Boc amine 1 wt % at 22° C. and stirred at 22-40° C. for 2-4 h. 0.36 volume 28% ammonium hydroxide was added over 2-4 h, then, 3.64 volumes 28% ammonium hydroxide was added over 4-10 h at 22-60° C. After cooling to 22° C., the batch was filtered, washed with 5:1 DMAc/water, then water. The wet cake was vacuum dried under nitrogen at ambient affording the product. Diastereoselectivity was ≥30:1.

Boc Deprotection of Formula Ia

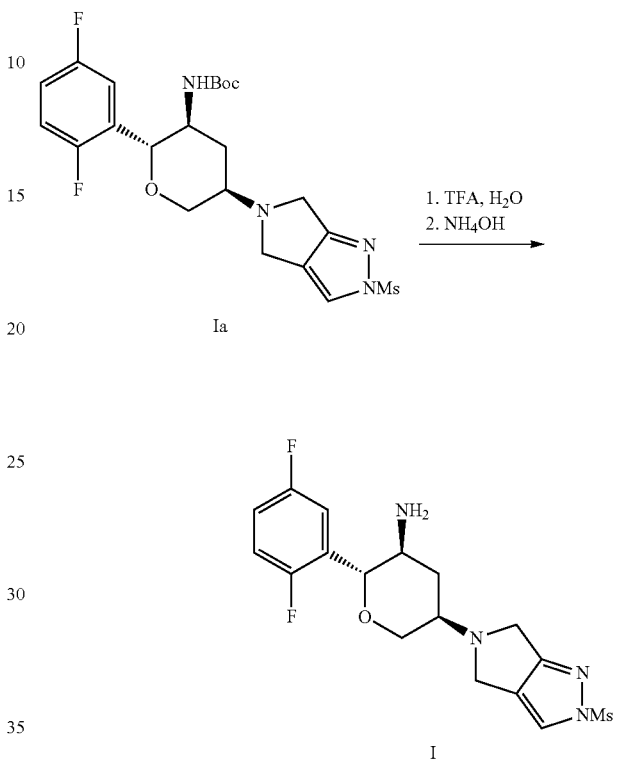

A reactor was charged with 2.5× (by volume) of trifluoroacetic acid. The batch was cooled to 5-10° C. The reactor was then charged with 0.4× (by volume) water. The batch was cooled to 0-5° C. The reactor was then charged with 1 equivalent (1 kg) of the compound of Formula Ia over 0.5-1 h while maintaining the temperature between 0-5° C. The reactor was then charged with 0.5× (by volume) trifluoroacetic acid to reactor while maintaining the temperature between 0-5° C. The batch was then heated between 15-20° C. and aged for 2-2.5 h. The batch was then cooled to between 5-10° C. A crystallizer was charged with water 5.0× (by volume) and 0.1× (by volume) of ammonia water and adjusted to between 3-13° C. To generate a seed bed, Compound I seed (1 wt % vs Ia) was added and the temperature as adjusted to between 3-13° C. A solution of ammonia water 3.8× (by volume) and of the compound of Formula Ia was added simultaneously to the seed bed over 2.5-3.5 hours while maintaining temperature at 3-13° C. and pH ~9-10. The batch was aged for at least 30 minutes and then filtered. The resulting crystals were washed with 3.0× (by volume) water at 3-13° C. twice and vacuum dried at ≤50° C. to afford the compound of formula I.

What is claimed is:

1. A process of preparing a compound of Formula 7

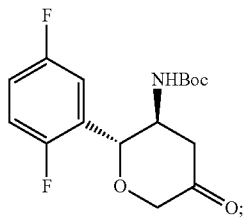

comprising reacting 2,4-difluorobenzaldehyde and nitromethane in the present of a copper salt, ligand, base and solvent to produce a compound of Formula 17:

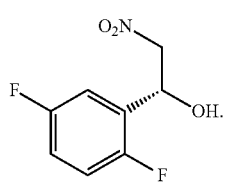

2. The process of claim 1 further comprising the step of reacting the compound of Formula 17 with acrolein in the presence of a base and solvent to produce a compound of Formula 18:

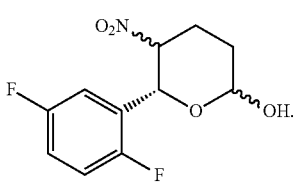

3. The process of claim 2 further comprising the step of reacting the compound of Formula 18 with a chlorinating agent in the presence of a base and a solvent to produce a compound of Formula 19:

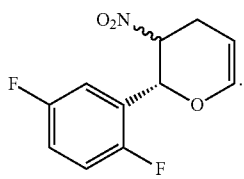

4. The process of claim 3 further comprising the step of crystallizing the compound of Formula 19 under basic conditions to produce a compound of Formula 19t:

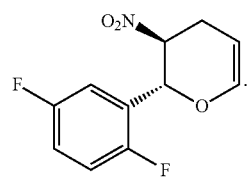

5. The process of claim 4 further comprising the steps of reacting the compound of Formula 19t with a hydrobrating agent and an oxidant to produce a compound of Formula 20:

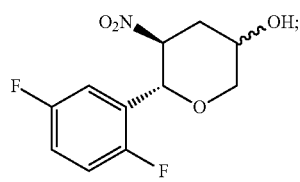

and reacting the compound of Formula 20 with a reducing agent and a protecting group to produce a compound of Formula 21:

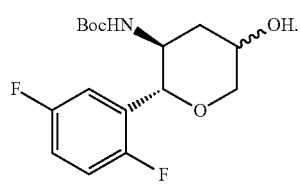

* * * * *